United States Patent [19]

Haber et al.

[11] 4,087,427
[45] May 2, 1978

[54] 2'-(5'-NITROFURYL)-SUBSTITUTED QUINOLINES AND PROCESS FOR PREPARING SAME

[76] Inventors: Raphael Ralph George Haber, 42 Kaplansky Street, Givatayim; Eva Schönberger, 38 Mivza Sinae Street, Ba-Yam, Ramat-Yosef, both of Israel

[21] Appl. No.: 643,830

[22] Filed: Jun. 6, 1967

[30] Foreign Application Priority Data

Jun. 23, 1966 Israel .................................. 26022

[51] Int. Cl.² .................. C07D 215/60; C07D 215/14
[52] U.S. Cl. ........................ 260/287 AR; 260/287 F; 260/287 L; 260/287 G; 260/287 CF; 260/288 CE; 260/288 CF; 260/289 C; 260/289 R; 260/289 N; 424/258
[58] Field of Search ............... 260/283, 286, 289, 287, 260/240 A, 287 AR, 287 G, 287 CE, 287 L, 288 CE, 289 R, 289 NA

[56] References Cited

U.S. PATENT DOCUMENTS

| 2,742,462 | 4/1956 | Geven ................................. 260/240 |
| 3,157,645 | 11/1964 | Spencer .............................. 260/240 |
| 3,272,828 | 9/1966 | Von Esch et al. ............ 260/287 CE |
| 3,349,095 | 10/1967 | Haber et al. .................. 260/347.8 C |
| 3,352,683 | 11/1967 | Schmidt et al. ................. 260/240 X |
| 3,374,239 | 3/1968 | Burch .................................... 260/287 |
| 3,475,421 | 10/1969 | Chretren et al. ............... 260/289 R |
| 3,496,066 | 2/1970 | Berger et al. .................... 260/289 R |

FOREIGN PATENT DOCUMENTS 1,443,177  9/1966  France .............................. 260/347.8

OTHER PUBLICATIONS

Burch; Chem. Abs., vol. 69; 59113s, (1968).

*Primary Examiner*—Donald G. Daus
*Assistant Examiner*—Mary Vaughn
*Attorney, Agent, or Firm*—Ostrolenk, Faber, Gerb & Soffin

[57] ABSTRACT 2- and 4-(5' nitrofuryl)quinoline derivatives which may be variously substituted on the quinoline nucleus have been found to possess excellent antibacterial and antifungal activity. Procedures for their manufacture are disclosed.

11 Claims, No Drawings

2'-(5'-NITROFURYL)-SUBSTITUTED QUINOLINES AND PROCESS FOR PREPARING SAME

The present invention relates to new nitrofuryl quinoline derivatives, to processes for their preparation and to compositions containing said nitrofuryl quinoline derivatives.

The present invention consists in nitrofuryl quinoline derivatives bearing at least in either the 2- or 4- position a 5-nitrofuryl group, which quinoline derivative may be further substituted; and their nitrogen oxides and non toxic acid-addition salts.

Suitable substitutents with which the new nitrofuryl quinoline derivatives according to the present invention may be substituted are, for example, lower alkyl ($C_1$-$C_5$) radicals, which may be further substituted, e.g. by halogen atoms, lower alkoxy ($C_1$-$C_5$) radicals, hydroxy, acyloxy, acyloxy- or hydroxy methyl and nitro groups; halogen atoms; carbonyl groups, their oximes or hydrazones; amino groups which may be further substituted, e.g. by substituted or unsubstituted lower alkyl radicals or by acyl radicals; cycloalkyl radicals and carboxyl and sulfonic acid groups and their esters and amides. Moreover, the 6 and 7 carbon atoms may together be part of a further aromatic or heteroaromatic nucleus which may be substituted.

Valuable nitrofuryl quinoline derivatives according to the present invention are, for example, compounds of general formula I

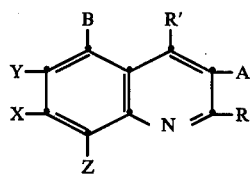

in which R stands for hydrogen, a 5-nitrofuryl group, a substituted or unsubstituted lower alkyl radical, an acyloxy- or hydroxy methyl group, a carbonyl group, its oxime or one of its hydrazones, and a carboxyl group or one of its esters or amides, R' stands for hydrogen, a 5-nitrofuryl group, an acyloxy- or hydroxy methyl group, a carbonyl group, is oxime or one of its hydrazones, or a substituted or unsubstituted lower alkyl- or amino radical, X stands for hydrogen, a halogen atom, a hydroxy or acyloxy group, a lower alkoxy radical, a substituted or unsubstituted lower alkyl- or amino-radical, Y stands for hydrogen or a substituted or unsubstituted lower alkyl radical, Z stands for hydrogen, a halogen atom, a nitro group or a substituted or unsubstituted lower alkyl- or amino radical, A stands for hydrogen or a substituted or unsubstituted lower alkyl radical, B stands for hydrogen, a nitro group or a substituted or unsubstituted amino radical, X and Y taken together may constitute part of an aromatic or heteroaromatic nucleus, which may be further substituted, at least one of substituents R or R' being a 5-nitrofuryl group.

The new nitrofuryl quinoline derivatives according to the present invention may be prepared by various processes. Some of them constitute also a part of the present invention.

Thus, certain of the new nitrofuryl quinoline derivatives bearing the 5-nitrofuryl group in the 4- position are prepared by the condensation of an 1-(5'-nitrofuryl)-1,3-diketobutane of general formula II (descried in French Pat. No. 1,443,177)

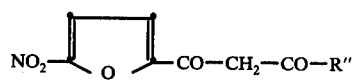

with a primary amine of general formula III $H_2NR'''$ to yield an anil of general formula IV

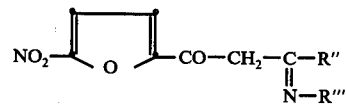

in which formulae R' stands for a substituted or unsubstituted lower alkyl radical and R''' stands for a substituted or unsubstituted phenyl radical, whereafter the anil compound of general formula IV is subjected to a ring closure treatment.

The condensation step is preferably carried out by either melting the reactants together in the presence of a catalyst, e.g. $ZnCl_2$ or by boiling said reactants together in an inert solvent, e.g. isopropanol. The anils of general formula IV are obtained by these methods in nearly theoretical yields.

The ring closure treatment is preferably carried out with concentrated sulfuric acid or with polyphosphoric acid at temperatures between 0° and 180° C.

The anils of general formula IV are also new compounds and constitute a part of the present invention.

Certain nitrofuryl quinoline derivatives bearing the 5-nitrofuryl group in 2- position are prepared by the condensation of a 5-nitrofuryl ketone of general formula V ("The Furans" by A. P. Dunlop and F. N. Peters, American Chemical Society Monograph Series, 1953, pages 429; 155)

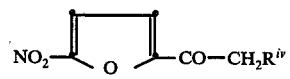

with a compound of general formula VI

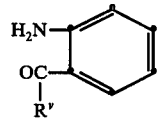

wherein the phenyl nucleus may be further substituted, in which formulae $R^{iv}$ stands for hydrogen or a substituted or unsubstituted lower alkyl radical and $R^v$ for hydrogen or a lower alkyl radical, in the presence of a catalyst, e.g. $ZnCl_2$, if desired, with the addition of a solvent, e.g. glacial acetic acid.

Further substituents may be introduced into the quinoline moiety in any suitable manner at any stage of the above or other processes. Eventually certain new nitrofuryl quinoline derivatives according to the present invention may be converted into other ones by methods known per se.

Thus, for example, alkyl radicals may be converted into halogenated alkyl radicals by way of halogenation, into a carbonyl group by way of oxidation, e.g. with selenium dioxide, or be converted into a carboxyl group by way of, for example oxidation, which carboxyl group in turn may be esterified.

The carbonyl group may be converted into the oxime by reaction with hydroxylamine and into a hydrazone by reaction with the appropriate hydrazine derivative.

The hydroxy group may be converted into the acyloxy group by way of esterification and vice versa the acyloxy group may be converted into the hydroxy group, by way of hydrolysis.

The nitrofuryl quinoline derivatives according to the present invention may be ring-nitrated with concentrated nitric acid without destroying either the furan nucleus or the quinoline nuclei.

The nitrofuryl quinoline derivatives according to the present invention may be converted into the corresponding nitrogen-oxides, and acid-addition salts by methods known per se. Thus, the nitrogen-oxide is prepared by oxidation of the appropriate nitrofuryl quinoline derivative with a suitable peroxide, e.g. hydrogen peroxide, and the acid-addition salt by the reaction with an appropriate acid.

A suitable process for the preparation of nitrofuryl quinoline derivatives bearing in the 4-position the 5-nitrofuryl group and in the 2-position an acyloxy- or hydroxymethyl group, consists in reacting the 2-methyl-4-[2'-(5'-nitrofuryl)]quinoline N-oxide with a carboxylic acid anhydride and, if desired, subjecting the product obtained to hydrolysis.

The new nitrofuryl quinoline derivatives according to the present invention have excellent antibacterial properties. They are also active antifungal agents and are relatively non-toxic. They may be used as therapeutic agents in the veterinary field and as fungicides in agriculture. Due to the broad spectrum activity against various types of bacteria and fungi the compounds described may be used with advantage in the external treatment of wounds.

The activity of some of the new nitrofuryl quinoline derivatives of the present invention is exemplified in Table I against a gram-positive (Staph. aureus), a gram-negative (Salmonella) bacterium and a fungus (Candida albicans). Table I indicates the minumum inhibitory concentration of the compound under reference in mg/100 cc required in order to inhibit the growth between 1 and 6 strains of each type. The measurements have been carried out by the conventional tube dilution method at 37° after 24 hours.

Table I

| Compound | Staph. aureus | Salmonella | Candida albicans |
|---|---|---|---|
| 2-Methyl-4-[2'-(5'-nitrofuryl)]quinoline | 0.01 | 0.5 | 0.5 |
| 2-Methyl-4-[2'-(5'-nitrofuryl)]-quinoline N-oxide | 0.02 | 1 | 0.1 |
| 2-Methyl-4-[2'-(5'-nitrofuryl)]-6-methyl quinoline | 0.01 | 0.5 | 0.5 |
| 2-Methyl-4-[2'-(5'-nitrofuryl)]-6-methyl quinoline N-oxide | 0.01 | >2.5 | 0.2–0.5 |
| 2-Methyl-4-[2'-(5'-nitrofuryl)]-7-chloro quinoline | 0.01 | 0.05 | 2.5 |
| 2-Methyl-4-[2'-(5'-nitrofuryl)]-7-chloro quinoline N-oxide | 0.025 | >2.5 | 0.2–0.5 |
| 2-Tribromomethyl-4-[2'-(5'-nitrofuryl)]-quinoline | 0.05 | >1 | 3–5 |
| 2-Carboxy-4-[2'-(5'-nitrofuryl)]quinoline | 0.1 | >1 | 3–5 |
| 2-Methyl-4-[2'-(5'-nitrofuryl)]-7-methoxy quinoline | 0.025 | 1 | 0.5 |
| 2-Methyl-4-[2'-(5'-nitrofuryl)]-7-methoxy quinoline N-oxide | 0.01 | 0.5 | 0.05 |
| 2-[2'-(5'-nitrofuryl)]-4-methyl-quinoline | 0.02– 0.05 | 0.5 | 0.05 |

Table I-continued

| Compound | Staph. aureus | Salmonella | Candida albicans |
|---|---|---|---|
| 2-[2'-(5'-nitrofuryl)]-4-methyl-quinoline N-oxide | 0.025 | 1 | 0.2–0.5 |
| 2-Methyl-4-[2'-(5'-nitrofuryl)]-6-ethyl quinoline | 0.01 | 2.5 | 2.5 |
| 2-Methyl-4-[2'-(5'-nitrofuryl)]-6,7-benzoquinoline | 0.5 | >1 | >5 |
| 2-Methyl-4-[2'-(5'-nitrofuryl)]-6-ethyl quinoline N-oxide | 0.05 | 2.5 | 0.2–0.5 |
| 2-Methyl-4-[2'-(5'-nitrofuryl)]-7-hydroxy quinoline | 0.01 | 0.5 | 1 |
| 2-Methyl-4-[2'-(5'-nitrofuryl)]-7-methyl quinoline | 0.005– 0.01 | 0.2– 0.5 | 0.3 |
| 2-Methyl-4-[2'-(5'-nitrofuryl)]-8-methyl quinoline | 0.03 | >5 | 0.5 |
| 2-Ethyl-4-[2'-(5'-nitrofuryl)]quinoline | 0.01 | >5 | 0.3 |
| 2-Ethyl-4-[2'-(5'-nitrofuryl)] quinoline N-oxide | 0.03 | 2.5– 5 | 0.3 |
| 2-Methyl-4-[2'-(5'-nitrofuryl)]-6,8-dimethyl quinoline | 0.005– 0.01 | >5 | >5 |
| 2-Tribromomethyl-4-[2'-(5'-nitrofuryl)]-6-methyl quinoline | 0.1 | >2.5 | >5 |
| 2-Methyl-4-[2'-(5'-nitrofuryl)]-7-acetoxy quinoline | 0.005 | 0.2– 0.5 | 1 |
| 2-Ethyl-4-[2'-(5'-nitrofuryl)]-6-ethyl quinoline | 0.005 | >1 | >5 |
| 2-Ethyl-4-[2'-(5'-nitrofuryl)]-6-ethyl quinoline N-oxide | 0.1 | >1 | 0.5–1 |
| 2-Ethyl-4-[2'-(5'-nitrofuryl)]-6-methyl quinoline | 0.005 | 1– >1 | <0.5 |
| 2-Ethyl-4-[2'-(5'-nitrofuryl)]-6-methyl quinoline N-oxide | 0.01 | | <0.5 |
| 2-[2'-(5'-nitrofuryl)]quinoline | 0.5 | 2.5 | 0.5 |
| 2-[2'-(5'-nitrofuryl)]quinoline N-oxide | 0.05 | >1 | <0.5 |
| 4-[2'-(5'-nitrofuryl)]-2-carboxaldehyde oxime | 0.05 | 0.5– 1 | 1 |

The new nitrofuryl quinoline derivatives according to the present invention may be prescribed to be taken per se, but are preferably prescribed in the form of tablets, capsules, ampules, ointments, tinctures or solutions, said preparations being prepared in a conventional manner, i.e. by the addition of suitable binders extenders, emulsifiers, solvents, other suitable therapeutic compounds and the like.

The new nitrofuryl quinoline derivatives of the present invention may also be used as feed additives. They may be either admixed directly with the feed, advantageously in an amount of about 0.001–1% of the total feed or as a part of a pre-mix. Such pre-mix may contain, besides the nitrofuryl quinoline derivative, any suitable carrier and/or feed additive, e.g. bentonite, $CaCO_3$, soyabean meal, corn meal and the like. The pre-mix should contain about 1–95% of the new compound.

The invention will be illustrated by the following Examples without being limited by them. All temperatures are indicated herein in ° C. All melting points are uncorrected.

EXAMPLE 1

5.91 g (0.03 moles) of 1-(5'-Nitrofuryl)-butane-1,3-dione and 2.8 g (0.03 moles) of freshly distilled aniline were heated together at 120° with a catalytic amount of $ZnCl_2$. A clear melt was obtained and after 15 minutes the whole mass solidified. The melt was kept for further 10 minutes at 120°. Thereafter it was cooled and recrystallised from methanol to yield 7.4 g of crystaline 1-(5'-nitro-2'-furo)-butanone-3-phenyl-imino of m.p. 127.5°–128.5°. Yield 87.5%.

Then, 5.6 g (0.02 moles) of the above Schiff base were dissolved at about 5° in 30 g of concentrated sulfuric acid. The clear solution obtained was allowed to reach room temperature, was thereafter heated for 10 minutes to 100°–110° and then poured on ice water.

An olive green precipitate was obtained which was filtered off and suspended in water. Ammonia was added to the suspension until the pH was slightly alkaline. The suspension was cooled and the precipitate obtained was filtered off to yield 2.4 of 2-methyl-4-[2'-(5'-nitrofuryl)]quinoline, m.p- 127°–130°. Further ammonia was added to the mother liquor to yield further 0.3 g of the above compound.

An analytical sample was obtained by recrystallisation from isopropanol/water; m.p. 138°–139°.

The analysis was calculated for $C_{14}H_{10}N_3O_3$: Calculated: C: 66.14%; H: 3.96%; N: 11.02%. Found: C: 66.08%; H: 4.10%; N: 10.98%.

2.7 g of the above quinoline derivative were dissolved with heating in 70 ml of glacial acetic acid, 2 ml of 30% hydrogen peroxide were added at once to the solution obtained, which was kept at 70° for 3 hours. Then water was added and the precipitate obtained was filtered off to yield 2.4 g of 2-methyl-4-[2'-(5'-nitrofuryl)] quinoline N-oxide, m.p. 207°.

An analytical sample was obtained by recrystallisation from isopropanol and nitromethane; m.p. 226°–227°.

The analysis was calculated for $C_{14}H_{10}N_2O_4$: Calculated: C: 62.22%; H: 3.73%; N: 10.37%. Found: C: 62.47%; H: 3.69%; N: 10.29%.

The hydro chloride of 2-methyl-4-[2'-(5'-nitrofuryl)]-quinoline has a m.p. of 190°–191.5°. The corresponding hydrobromide has m.p. 230.5°–231°.

EXAMPLE 2

3 g (0.02 mole) of 5-Nitrofuryl methyl ketone and 2.7 g (0.02 mole) of o-amino acetophenone were heated together with a catalytic amount of $ZnCl_2$ at 150°. The clear melt obtained was heated for 1 hour at 140°–150°, then cooled and dissolved in isopropanol. The solution was filtered through charcoal. The filtrate was concentrated and cooled to yield 1.53 g (30%) of 2-[2'-(5-nitrofuryl)]-4-methyl quinoline, m.p. 148°–162°.

An analytical sample was obtained by consecutive recrystallisation from acetone, isopropanol and benzene/petrol-ether; m.p. 167°–168°.

The analysis was calculated for $C_{14}H_{10}N_2O_3$: Calculated: C: 66.14%; H: 3.96%; N: 11.02%. Found: C: 65.94%; H: 4.14%; N: 10.98%.

The N-oxide had a m.p. of 210°–212°.

EXAMPLE 3

5.91 g (0.03 mole) of 1-(5'-Nitrofuryl)-2,4-butanedione and 3.82 g (0.03 mole) of m-chloroaniline were melted together with a catalytic amount of $ZnCl_2$ in an open vessel at 110°–120°. After 10 minutes the heating was stopped, the mixture was cooled and dissolved in nitromethane. The solution obtained was filtered hot and the filtrate yielded after cooling 8.9 g (97% yield) of crystaline 1-(5'-nitro-2'-furo)butanone-3-(m-chlorophenyl) imino, m.p. 161°–162°.

6 g of the above enamine were added gradually with cooling to 18 ml of cooled concentrated sulfuric acid. The mixture was allowed to reach room temperature and then heated for 10 minutes to 100°–110°. The mixture was then cooled and poured on ice-water. The amorphous precipitate obtained was filtered off, washed with water, resuspended in water and the suspension was made alkaline with ammonia to yield 5.5 g (yield 97%) of 2-methyl-4-[2'-(5'-nitrofuryl]-7-chloro quinoline.

An analytical sample was obtained by recrystallisation from isopropanol and acetone/water; m.p. 146°.

The analysis was calculated for $C_{14}H_9N_3O_3Cl$: Calculated: C: 58.23%; H: 3.14%; N: 9.70%; Cl: 12.30%. Found: C: 58.33%; H: 3.08%; N: 9.53%; Cl: 12.26%. 1.2 g of the above quinoline derivative were dissolved with heating in 25 ml of glacial acetic acid. 2 ml of 30% hydrogen peroxide were added to the solution, which was kept for 5 hours at 70°. Water was added and the precipitate obtained was filtered off to yield 1.15 g (yield 91%) of 2-methyl-4-[2'-(5'-nitrofuryl)]-7-chloro-quinoline N-oxide, m.p. 198°–204°.

An analytical sample was obtained by recrystallisation from nitromethane; m.p. 205°–206°. The analysis was calculated for $C_{14}H_9N_2O_4Cl$: Calculated: C: 55.20%; H: 2.98%; N: 9.19%. Found: C: 55.15%; H: 3.09%; N: 9.13%.

EXAMPLE 4

5.91 g (0.03 mole) of 1-(5'-Nitrofuryl)-2,4-butanedione and 3.9 g (0.03 mole) of m-aminophenol were heated together with a catalytic amount of $ZnCl_2$ at 90°. The clear melt obtained was heated for 10 minutes at 100°–110°, then cooled and recrystallised from methanol to yield 6.1 g of 1-(5'-nitro-2'-furo)butanone-3-(m-hydroxy-phenyl) imino; m.p. 190.5°–192°.

6 g of the above Schiff base were dissolved in 36 g of sulfuric acid at about 5°. The reaction mixture was kept for 5 days at room temperature and then poured on ice-water. The aqueous suspension obtained was neutralised with ammonia and the precipitated crystals were filtered off and recrystallised from ethanol to yield bright-yellow crystals of 2-methyl-4-[2'-(5'-nitrofuryl)]-7-hydroxy quinoline; m.p. 259°.

An analytical sample was obtained by repeated recrystallisation from ethanol and nitromethane; m.p. 272°(decomp.).

The analysis was calculated for $C_{14}H_{10}N_2O_4$ Calculated: C: 62.22%; H: 3.73%; N: 10.37%. Found: C: 62.03% H: 3.92% N: 10.20%.

2-methyl-4-[2'-(5'-nitrofuryl)]-7-hydroxy quinoline N-oxide was prepared by oxidation of the above compound with $H_2O_2$ 30% in acetic acid glacial. M.p. 293° (decomp).

The analysis was calculated for $C_{14}H_{10}N_2O_5$: Calculated: C: 58.75%; H: 3.52%; N: 9.79%. Found: C: 58.88%; H: 3.59%; N: 9.80%.

EXAMPLE 5

2 g of 2-Methyl-4-[2'-(5'-nitrofuryl)]quinoline, prepared as described in Example 1, were dissolved with heating in 20 ml of glacial acetic acid. 4.0 g of anhydrous sodium acetate and thereafter 1.25 ml of bromine dissolved in some acetic acid were added at 70°–75°. The reaction mixture was then heated for 90 minutes at 90°–95°, then cooled and the precipitate obtained was filtered off to yield 3.6 g (yield 92%) of yellow crystals of 2-tribromomethyl-4-[2'-(5'-nitrofuryl)]quinoline; m.p. 154°–155°.

An analytical sample was obtained by recrystallisation from isopropanol; m.p. 158°–160°.

The analysis was calculated for $C_{14}H_7N_2O_3Br_3$: Calculated: C: 34.25%; H: 1.44%; N: 5.70%; Br: 48.83%. Found: C: 34.38%; H: 1.45%; N: 5.90%; Br: 49.03%.

EXAMPLE 6

1.5 g of 2-Tribromomethyl-4-[2'-(5'-nitrofuryl)]quinoline, prepared as described in Example 5, were dissolved in 50 ml of 50% sulfuric acid. Catalytic quantities of $FeCl_3$ were added to the solution obtained, which was then kept for 20 hours at 110°–130°. The clear solution was cooled, water was added and the precipitate obtained was filtered off to yield 0.4 g of 2-carboxy-4-[2'-(5'-nitrofuryl)]quinoline; m.p. 190°–193°.

An analytical sample was obtained by recrystallisation from glacial acetic acid; m.p. 200°.

The analysis was calculated for $C_{14}H_8N_2O_5$: Calculated: C: 59.16%; H: 2.84%; N: 9.86%. Found: C: 59.21%; H: 2.85%; N: 9.52%.

EXAMPLE 7

5.91 g (0.03 mole) of 1-(5'-Nitrofuryl)-2,4-butanedione and 3.7 g (0.03 mole) of m-anisine were heated together with a catalytic amount of $ZnCl_2$ for 10 minutes at 110°. After cooling and recrystallisation from methanol, 1-(5'-nitro-2'-furo)-butanone-3-(m-methoxyphenyl) imino was obtained, yield 81%; m.p. 137°.

The above enamine was subjected to a ring closure treatment similar to that described in Example 1 to yield 2-methyl-4-[2'-(5'-nitrofuryl)]-7-methoxy quinoline, yield 54%; m.p. 146°–148.5°.

An analytical sample was obtained by recrystallisation from isopropanol; m.p. 156°–157°.

The analysis was calculated for $C_{15}H_{12}N_2O_4$ Calculated: C: 63.38%; H: 4.25%; N: 9.85%. Found: C: 63.25%; H: 4.38%; N: 9.83%.

The N-oxide was prepared by oxidation with $H_2O_2$; m.p. 207°–208°.

EXAMPLE 8

19.7 g (0.1 mole) of 1-(5'-Nitrofuryl)-2,4-butanedione and 10.7 g (0.1 mole) of p-toluidine were heated together with a catalytic amount of $ZnCl_2$ at 120°. After 10 minutes of further heating and working up as described in Example 1, 1-nitro-2'-furo)-butanone-3-(p-methyl-phenyl) imino was obtained, yield 98%, m.p. 145°–146°.

The above enamine was subjected to a ring closure treatment similar to that described in Example 1 to yield 2-methyl-4-[2'-(5'-nitrofuryl)]-6-methyl quinoline, yield 97%; m.p. 146°–148°.

An analytical sample was obtained by recrstallisation from isopropanol; m.p. 151°.

The analysis was calculated for $C_{15}H_{12}N_2O_3$: Calculated: C: 67.12%; H: 4.51; N: 10.44%. Found: C: 67.08%; H: 4.57%; N: 10.57%.

The N-oxide was prepared by oxidation with $H_2O_2$; m.p. 227°–229° (after recrystallisation).

The analysis was calculated for $C_{15}H_{12}N_2O_4$: Calculated: C: 63.38%; H: 4.25%; N: 9.85%. Found: C: 63.60%; H: 4.41%; N: 9.74%.

EXAMPLE 9

2.8 g (0.01 mole) of 2-methyl-4-[2'-(5'-nitrofuryl)]-7-chloro quinoline, prepared as described in Example 3, were added gradually with cooling to 8 ml of a concentrated sulfuric acid, the temperature being maintained below 0°. 0.6 ml of nitric acid (100%) was added in one portion to the mixture at said temperature. The mixture was then allowed to reach room temperature, kept at said temperature for 3 hours and then poured on ice-water. The amorphous precipitate obtained was filtered off, washed with water and dissolved in ethanol. The solution obtained was filtered with charcoal, concentrated and cooled to yield 1.1 g of 2-methyl-4-[2'-(5'-nitrofuryl)]-7-chloro-8-nitro quinoline; m.p. 198°–202°.

An analytical sample was obtained by recrystallisation from isopropanol and nitromethane; m.p. 207°–208°.

The analysis was calculated for $C_{14}H_8N_3O_5Cl$: Calculated: C: 50.39%; H: 2.42%; Cl: 10.63%. Found: C: 50.15%; H: 2.51%; Cl: 10.43%.

There was similarly 2,8-dimethyl-4-[2'-(5'-nitrofuryl]-5-nitroquinoline, m.p. 229°–232°.

EXAMPLE 10

Performing the process as described in Example 8, but replacing the p-toluidine by o-toluidine 1-(5'nitro-2'-furo)-butanone-3-(o-methyl-phenyl) imino was obtained, yield 91.5%; m.p. 127°–129°.

The enamine was subjected to a ring closure treatment similar to that described in Example 1 to yield 2,8-dimethyl-4-[2'-(5'-nitrofuryl)]quinoline, yield 82%; m.p. 147°–149°.

An analytical sample was obtained by recrystallisation from isopropanol and nitromethane; m.p. 157°–158.5°.

The analysis was calculated for $C_{15}H_{12}N_2O_3$: Calculated: C: 67.12%; H: 4.51%; N: 10.44%. Found: C: 67.05%; H: 4.36%; N: 10.52.

The N-oxide of the above compound was prepared by oxidation with peracetic acid in glacial acetic acid. The melting point of the crude compound was 149°–151°.

An analytical sample was prepared by recrystallisations from isopropanol yielding a compound melting at 158°–160°.

The analysis was calculated for $C_{15}H_{12}N_2O_4$: Calculated: C: 63.38%; H: 4.25%. Found: C: 63.59%; H: 4.43%.

EXAMPLE 11

Performing the process as described in Example 8, but replacing the p-toluidine by m-toluidine, 1-(5'-nitro-2'-furo)-butanone-3-(m-methyl-phenyl) imino was obtained, yield 90.5%; m.p. 146°–147.5°.

The enamine was subjected to a ring closure treatment similar to that described in Example 1 to yield 2,7-dimethyl-4-[2'-(5'-nitrofuryl)]quinoline, yield 75%; m.p. 142°–145°.

An analytical sample was obtained by recrystallisation from isopropanol and nitromethane; m.p. 145°–146°.

The analysis was calculated for $C_{15}H_{12}N_2O_3$: Calculated: C: 67.12%; H: 4.51%; N: 10.44%. Found: C: 67.04%; H: 4.45%; N: 10.67%.

The N-oxide of the above compound was prepared by an oxidation reaction with $H_2O_2$ in glacial acetic acid. Yield 92%, m.p. 210°–212°.

An analytical sample was prepared by recrystallisation from ethoxy ethanol and nitromethane; m.p. 217°–218.5°.

The analysis was calculated for $C_{15}H_{12}N_2O_4$: Calculated: C: 63.38%; H: 4.25%; N: 9.85%. Found: C: 63.22%; H: 4.41%; N: 10.07%.

EXAMPLE 12

1.27 g of 2-methyl-4-[2'-(5'-nitrofuryl)]quinoline, prepared as described in Example 1, was dissolved in 13 ml of hot acetic acid. 0.45 g of anhydrous sodium acetate was added to the solution obtained and then 0.8 g of bromine dissolved in 2 ml of acetic acid was added dropwise in the course of 15 minutes. The reaction mixture was then cooled and the crystals obtained filtered off. Thin layer chromatography showed that the material obtained was a mixture of 2-dibromo- and 2-tribromo-methyl-4-[2'-(5'-nitrofuryl)]quinoline.

The material was recrystallised in success ion from ethanol, isopropanol, cellosolve and again isopropanol to yield the dibromo-compound only; m.p. 187.5°–189°.

The analysis was calculated for $C_{14}H_8N_2O_3Br_2$: Calculated: C: 40.80%; H: 1.95%; N: 6.80%; Br: 38.90%. Found: C: 40.60%; H: 2.20%; N: 6.63%; Br: 38.64%.

EXAMPLE 13

2.54 g (0.01 mole) of 2-Methyl-4-[2'-(5'-nitrofuryl)]-quinoline, prepared as described in Example 1, and 1.5 g of sodium carbonate were suspended in 80 ml of benzene. The mixture was heated to 70° and chlorine gas was bubbled therethrough in the course of 3 hours. After cooling, some unreacted starting material was filtered off and the filtrate was concentrated to yield 2-trichloromethyl-4-[2'-(5'-nitrofuryl)]quinoline; m.p. 142°–144°.

An analytical sample was obtained by recrystallisation from isopropanol and nitromethane; m.p. 145°–146°.

The analysis was calculated for $C_{14}H_7N_2O_3Cl_3$: Calculated: C: 47.02%; H: 1.98%; N: 7.83%; Cl: 29.73%. Found: C: 47.03%; H: 2.13%; N: 7.70%; Cl: 29.51%.

EXAMPLE 14

1.97 g (0.01 mole) of 1-(5'-nitrofuryl)-2,4-butanedione and 1.43 g (0.01 mole) of β-naphthylamine were heated together with a catalytic amount of $ZnCl_2$ for 10 minutes at 100°–110°. After cooling and recrystallisation 2.65 g (yield 82.5% of 1-(5'-nitro-2'-furo)-butanone-3-naphthyl imino were obtained; m.p. 184°–186.5°.

The enamine obtained was heated with 6 times its weight of concentrated sulfuric acid for 10 minutes at 110°. After cooling the reaction mixture was poured on ice-water, neutralised and the precipitate obtained filtered off to yield 2-methyl-4-[2'-(5'-nitrofuryl)]-6,7-benzoquinoline; m.p. 221°.

An analytical sample was obtained by recrystallisation from nitromethane; m.p. 228°.

The analysis was calculated for $C_{18}H_{12}N_2O_3$: Calculated: C: 71.05%; H: 3.97%; N: 9.21%. Found: C: 71.21%; H: 3.96%; N: 8.98%.

The N-oxide was prepared by oxidation with $H_2O_2$ in glacial acetic acid, yield 98%, m.p. 230°–235°.

An analytical sample was prepared by recrystallisation from nitromethane, m.p. 241°–243°.

The analysis was calculated for $C_{18}H_{12}N_2O_4$. Calculated: C: 67.50%; H: 3.78%; N: 8.75%. Found: C: 67.33%; H: 3.94%; N: 8.76%.

EXAMPLE 15

2.7 g (0.01 mole) of 2-Methyl-4-[2'-(5'-nitrofuryl)]-6-methyl quinoline, prepared as described in Example 8, were dissolved in 35 ml of acetic acid at 70°. At the same temperature were added 5.4 g of anhydrous sodium acetate and thereafter in the course of 25 minutes 2.4 g of bromine dissolved in 5 ml of glacial acetic acid. The mixture was then heated for 1 hour at 90°–95°, then cooled and the precipitate obtained was filtered off to yield 2.7 g of yellow-green crystals of 2-tribromomethyl-4-[2'-(5'-nitrofuryl)]-6-methyl quinoline; m.p. 191.5°–193°.

An analytical sample was obtained by recrystallisations from isopropanol, dioxane and nitromethane; m.p. 193°–195°.

The analysis was calculated for $C_{15}H_9N_2O_3Br_3$: Calculated: C: 35.60%; H: 1.78%; N: 5.54%; Br: 47.52%. Found: C: 35.74%; H: 2.03%; N: 5.35%; Br: 47.55%.

EXAMPLE 16

Performing the process as described in Example 2, but replacing the o-amino acetophenone by o-amino benzaldehyde, 2-[2'-(5'-nitrofuryl)]quinoline was obtained; m.p. 137°–147°.

An analytical sample was obtained by consecutive recrystallisation from methanol, isopropanol and ethoxy-ethanol; m.p. 196°–198°.

The analysis was calculated for $C_{13}H_8N_2O_3$: Calculated: C: 65.00%; H: 3.36%; N: 11.66%. Found: C: 64.82%; H: 3.32%; N: 11.92%.

The N-oxide had a m.p. of 215°–216°.

EXAMPLE 17

Performing the process as described in Example 2 but utilising as starting materials 5-nitrofuryl ethyl ketone and o-amino benzaldehyde, 2-[2'-(5'-nitrofuryl)]-3-methyl quinoline was obtained; m.p. 175°–196°.

EXAMPLE 18

2.54 g (0.01 mole) of 2-methyl-4-[2'-(5'-nitrofuryl)]-quinoline, prepared as described in Example 1, were added gradually with cooling to 8 ml of concentrated sulfuric acid, the temperature being maintained below 0°. 0.6 ml of nitric acid (100%) were added at said temperature in one portion. The mixture was then allowed to reach room temperature, kept at that temperature for 3 hours and then poured on ice-water. The precipitate obtained was filtered off, washed with water to yield 1.8 g of yellow crystals, m.p. 121°–157°.

Thin layer chromatography showed 2 spots corresponding to 2-methyl-4-[2'-(5'-nitrofuryl)]-5- and 8-nitro quinoline.

The recrystallised material had a m.p. of 193°–198°.

The analysis was calculated for $C_{14}H_9N_3O_5$: Calculated: C: 56.19%; H: 3.03%. Found: C: 56.36%; H: 3.04%.

EXAMPLE 19

In a manner similarly to that described in Example 1 there were prepared:

a. 2-methyl-4-[2'-(5'-nitrofuryl)]-6-ethyl quinoline. m.p. 114°–115°.

The analysis was calculated for $C_{16}H_{14}N_2O_3$: Calculated: C: 68.08%; H: 5.00%; N: 9.92%. Found: C: 68.05%; H: 5.16%; N: 10.24%.

The corresponding N-oxide was prepared m.p. 194°–195°.

The analysis was calculated for $C_{16}H_{14}N_2O_4$. Calculated: C: 64.42%; H: 4.73%; N: 9.39%. Found: C: 64.37%; H: 4.94%; N: 9.20%.

b. 2,6,8-trimethyl-4-[2'-(5'-nitrofuryl)]quinoline. m.p. 143°–143,5°.

The analysis was calculated for $C_{16}H_{14}N_2O_3$: Calculated: C: 68.08%; H: 5.00%; N: 9.92%. Found: C: 67.88%; H: 5.28%; N: 10.00%.

c. 2,5,8-trimethyl-4-[2'-(5'-nitrofuryl)]quinoline m.p. 133°–134°.

The analysis was calculated for $C_{16}H_{14}N_2O_3$: Calculated: C: 68.08%; H: 5.00%; N: 9.92%. Found: C: 68.39%; H: 4.91%; N: 9.72%.

d. 2-methyl-4-[2'-(5'-nitrofuryl)]-5,8-dimethoxy quinoline m.p. 183°–183.5°.

The analysis was calculated for $C_{16}H_{14}N_2O_5$: Calculated: C: 61.14%; H: 4.49%; N: 8.91%. Found: C: 61.05%; H: 4.63%; N: 8.73%.

EXAMPLE 20

Performing the process as described in example 1 but replacing the 1-(5'-nitrofuryl)-butane-1,3-dione by 1-(5'-nitrofuryl)-pentane-1,3-dione. The following 5-nitrofuryl quinolines were prepared:

a. 2-ethyl-4-[2'-(5'-nitrofuryl)]quinoline m.p. 127°–128°.

The analysis was calculated for $C_{15}H_{12}N_2O_3$: Calculated: C: 67.16%; H: 4.51%; N: 10.44%. Found: C: 67.42%; H: 4.70%; N: 10.27%.

The corresponding N-oxide has a m.p. of 184.5°–185.5°.

b. 2-ethyl-4-[2'-(5'-nitrofuryl)]-6-ethyl quinoline m.p. 117.5°–118.5°.

The analysis was calculated for $C_{17}H_{16}N_2O_3$: Calculated: C: 68.91%; H: 5.44%; N: 9.45%. Found: C: 69.09%; H: 5.56%; N: 9.37%.

The corresponding N-oxide was prepared, m.p. 173.5°–174.5°.

c. 2-ethyl-4-[2'-(5'-nitrofuryl)]-6-methyl quinoline m.p. 112.5°–113.5.

The analysis was calculated for $C_{16}H_{14}N_2O_3$: Calculated: C: 68.08%; H: 5.00%; N: 9.92%. Found: C: 68.21%; H: 5.13%; N: 10.05%.

The corresponding N-oxide was prepared, m.p. 158.5°–159.5°.

EXAMPLE 21

A mixture comprising 2 g of 2-methyl-4-[2'-(5'-nitrofuryl)]-7-hydroxy quinoline, prepared as described in Example 4, 40 ml of acetic anhydride and 1 ml of concentrated sulfuric acid were refluxed for 2 hours, then left to cool to room temperature and finally poured on ice water. After 2 hours of further stirring the brown crystals obtained were filtered off and washed throughly with water.

1.5 g of 2-methyl-4-[2'-(5'-nitrofuryl)]-7-acetoxy-quinoline were obtained., yield 65%

An analytical sample was prepared by repeated recrystallisation from dioxane, nitromethane and isopropanol, m.p. 171.5°–172.5°.

The analysis was calculated for $C_{16}H_{12}N_2O_5$: Calculated: C: 61.54%; H: 3.87%; N: 8.97%. Found: C: 61.37%; H: 3.83%; N: 9.01%.

The N-oxide of the above compound was prepared as described in previous examples, m.p. 176°.

EXAMPLE 22

19.7 g of 1-(5'-nitrofuryl)-2,4-butanedione and 13.7 g of m-phenetidine were heated for 20 minutes together with a catalytic amount of $ZnCl_2$ at 110°–120°. The mixture was then cooled and recrystallised from methanol to yield 28.5 g of 1-(5'-nitro-2'-furo)-butanone-3-(m-ethoxy-phenyl)imino, m.p. 129°–130°.

2 g of the above Schiff base were mixed with 25 g of polyphosphoric acid at about 5° C. The reaction mixture was a viscous mass which was heated for 10 minutes at 100°, then allowed to cool to room temperature and then 100 ml of water were added with external cooling. The pH was adjusted to 8, with ammonium hydroxide and the greenish crystals obtained were filtered off and washed with water. 1.7 g of the crude compound obtained, 2-methyl-4-[2'-(5'-nitrofuryl)]-7-ethoxy quinoline were recrystallised from ethanol 95%, m.p. 122.5°–123.5°.

An analytical sample was prepared by successive recrystallisation from isopropanol, acetone/water and cellosolve. m.p. 124.5°–126.5°.

The N-oxide of the above compound was prepared by oxidation with $H_2O_2$ 30% in glacial acetic acid.

An analytical sample was prepared by repeated recrystallisations from nitromethane and ethanol, m.p. 201°–202°.

The analysis was calculated for $C_{16}H_{14}N_2O_5$: Calculated: C: 61.14%; H: 4.49%; N: 8.91%. Found: C: 60.99%; H: 4.61%; N: 8.84%.

EXAMPLE 23

A mixture of 2 g of 2-methyl-4-[2'-(5'-nitrofuryl)]-quinoline N-oxide prepared as described in Example 1 and 10 g of acetic acid anhydride was heated to 120°–130° for 2 hours on an oil-bath. The excess of acetic acid anhydride was then distilled off under reduced pressure and ice-water was added to the residue. Crystals precipitated which were separated by filtration and washed with water.

2.1 g of 2-acetoxymethyl-4-[2'-(5'-nitrofuryl)]quinoline were obtained; yield 89%, m.p. 125°–130°. After recrystallisation from ethanol with charcoal the melting point rose to 135°–136°.

An analytical sample having a m.p. 137°–138° was prepared.

The analysis was calculated for $C_{16}H_{12}N_2O_5$: Calculated: C: 61.54%; H: 3.87%; N: 8.97%. Found: C: 61.44%; H: 3.92%; N: 9.00%.

The N-oxide of the above compound was prepared by oxidation with hydrogen peroxide dissolved in glacial acetic acid yielding a compound melting at 188°–189.5° after recrystallisation from isopropanol.

2-Hydroxymethyl-4-[2'-(5'-nitrofuryl)]quinoline was prepared by refluxing the 2-acetoxy-methyl-4-[2'-(5'-nitrofuryl)]quinoline in a 12% sulfuric acid solution.

EXAMPLE 24

In the same manner as described in Example 23 there was prepared from 2-methyl-4-[2'-(5'-nitrofuryl)]-7-hydroxyquinoline N-oxide the 2-acetoxymethyl-4-[2'-(5'-nitrofuryl)]-7-acetoxy quinoline, m.p. 151.5°–152°.

The analysis was calculated for $C_{18}H_{14}N_2O_7$: Calculated: C: 58.38%; H: 3.81%; N: 7.56%. Found: C: 58.41%; H: 4.04%; N: 7.72%.

EXAMPLE 25

In a 250 ml three necked, round-bottomed flask, fitted with stirrer and reflux condenser were placed 20 ml of dioxane 90% and 3.9 g of selenium dioxide. The mixture was heated to 50°–60° until the solid was dissolved. Then 5 g of 2-methyl-4-[2'-(5'-nitrofuryl)]quinoline (prepared as described in Example 1) were added to the solution in one lot and the resulting mixture was refluxed for 2 hours with continued stirring. The hot solution was then twice filtered with charcoal, and concentrated to ½ of its initial volume. The precipitated crystals of 4-[2'-(5'-nitrofuryl)]quinoline-2-carboxaldehyde, were then filtered off.

The crude compound was recrystallised from dioxane, yielding 4.2 g of a yellow compound, m.p. 185°–187°.

Similarly from 2-ethyl-4-[2'-(5'-nitrofuryl)]quinoline there was prepared 4-[2'-(5'-nitrofuryl)]quinoline-2-methyl ketone, m.p. 209°–211°.

EXAMPLE 26

In a 100 ml three necked, round bottomed flask fitted with stirrer, and reflux condenser, were placed 2.7 g of 4-[2'-(5'-nitrofuryl)]quinoline-2-carboxaldehyde and 50 ml of dioxane. The mixture was heated to boiling until a clear solution was obtained. Then were added at once 0.7 g hydroxylamine hydrochloride dissolved in 20 ml water. The mixture was refluxed with stirring for 2 hours. The hot solution was filtered with charcoal and concentrated to 1/5 of its initial volume. 50 ml of water were added and the crystaline precipitate was filtered off. 2.6 g of 4-[2'-(5'-nitrofuryl)]quinoline-2-carboxaldehyde oxime were obtained. Yield 92% m.p. 202.5°–204°.

An analytical sample was obtained by successive recrystallisation from isopropanol, nitromethane and acetone, m.p. 208°–210°.

The analysis was calculated for $C_{14}H_9N_3O_4$: Calculated: C: 59.37%; H: 3.20%; N: 14.84%. Found: C: 59.23%; H: 3.33%; N: 14.68%.

The N-oxide of the above compound was prepared by the usual manner, i.e. by oxidation with $H_2O_2$ 30% in glacial acetic acid, m.p. 201.5°–203.5°.

The analysis was calculated for $C_{14}H_9N_3O_5$: Calculated: C: 56.19%; H: 3.03%; N: 14.04%. Found: C: 56.33%; H: 3.17; N: 13.94%.

EXAMPLE 27

In the same manner as described in Example 26 replacing the hydroxylamine hydrochloride by semicarbazide hydrochloride there was obtained 4-[2'-(5'-nitrofuryl)]quinoline-2-carboxaldehyde semicarbazone.

An analytical sample was prepared by successive recrystallisat on from isopropanol, acetone and dioxane, m.p. 247°–248°.

The analysis was calculated for $C_{15}H_{11}H_5O_4$: Calculated: C: 55.39%; H: 3.41%; N: 21.53%. Found: C: 55.54%; H: 4.03%; N: 21.34%.

EXAMPLE 28

In the same manner as described in Example 26 replacing the hydroxylamine hydrochloride by 1-amino-oxazolidine-2-one there was obtained 4-[2'-(5'-nitrofuryl)]quinoline-2-carboxaldehyde-amino-oxazolidone, m.p. 264°–265.5°.

The analysis was calculated for $C_{17}H_{12}N_4O_5$: Calculated: C: 57.96%; H: 3.34%; N: 15.90%. Found: C: 57.83%; H: 3.45%; N: 15.93%.

EXAMPLE 29

In the same manner as described in Example 26 replacing the hydroxylamine hydrochloride by 1-aminohydantoin there was obtained 4-[2'-(5'-nitrofuryl)]quinoline-2-carboxaldehyde aminohydantoin, m.p. 233°–235°.

Likewise in the same manner as described in Example 26 replacing the hydroxylamine hydrochloride by acetylhydrazine, phenylhydrazine or isonicotinoyl hydrazide there was obtained acetyl hydrazone, phenylhydrazone and isonicotinoyl hydrazone, respectively, of the 4-[2'-(5'-nitrofuryl)]quinoline-2-carboxaldehyde.

EXAMPLE 30

4-[2'-(5'-nitrofuryl)]quinoline-2-carboxaldehyde prepared as described in Example 25 was oxidised with $H_2O_2$ glacial acetic acid to yield 2-carboxy-4-[2'-(5'-nitrofuryl]quinoline, yield 85%, m.p. crude 192°–196°; after recrystallisation from isopropanol, nitromethane the melting point was 199.5°–200°.

A mixed melting point determination with the compound prepared in Example 6 gave no depression.

EXAMPLE 31

A mixture of

| | |
|---|---|
| Polyethylene glycol 4000 | 200 g |
| Polyethylene glycol 1500 | 200 g |
| Polyethylene glycol 300 | 250 g |
| Propylene glycol | 125 g |
| Cetyl alcohol | 20 g | was heated on a steam bath. 2–3 g of 2-Methyl-4-[2'-(5'-nitrofuryl)]quinoline, prepared as described in Example 1, were added to the melt with efficient stirring. After cooling the mass obtained was passed through an ointment roller to obtain an ointment.

EXAMPLE 2

16 g of 4-methyl-2-[2'-(5'-nitrofuryl)]quinoline, prepared as described in Example 2, and 25 g of lactose were mixed together. A starch mucilage binder was added in an amount sufficient to produce a proper mass for granulation. The mass obtained was passed through a sieve, dried at 70°–80° and then again passed through a sieve. A small quantity of talcum and starch power was added and tablets were pressed in a tabletting machine.

EXAMPLE 33

A mixture of 1 g of 2-methyl-4-[2'-(5'-nitrofuryl)]-7-methoxy quinoline N-oxide, prepared as described in Example 7, 4 g of lactose, 6 g of calcium carbonate and 50 g of soyabean meal were mixed in a Fisher-Kendall mixer to be utilised as premix for animal feedstuffs.

We claim:

1. A quinoline compound directly linked at one of the 2- and 4- carbons to a 2'-(5'-nitrofuryl) group and substituted at the other of said carbons by a substituent selected from the group consisting of methyl ketone, carboxaldehyde, carboxaldehyde oxime, carboxaldehyde hydrazone, carboxaldehyde semicarbazide, carboxaldehyde amino-oxazolidine, and carboxaldehyde amino-hydantoin; and the N-oxide and non-toxic acid addition salts of such compound.

2. A compound according to claim 1, wherein the 5'-nitrofuryl group is attached to the 4-carbon.

3. A compound according to claim 1, wherein said substituent is carboxaldehyde.

4. A compound according to claim 2, wherein the substituent at the 2-position is carboxaldehyde oxime or its N-oxide.

5. A compound according to claim 2, wherein the substituent at the 2-position is carboxaldehyde semicarbazone.

6. A compound according to claim 2, wherein the substituent at the 2-position is carboxaldehyde amino-oxazolidone.

7. A compound according to claim 2, wherein the substituent at the 2-position is carboxaldehyde-aminohydantoin.

8. A compound according to claim 2, wherein the substituent at the 2-position is carboxaldehyde-acetylhydrazone.

9. A compound according to claim 2, wherein the substituent at the 2-position is carboxaldehyde-phenylhydrazone.

10. A compound according to claim 2, wherein the substituent at the 2-position is carboxaldehyde isonicotinoyl hydrazone.

11. A compound according to claim 2, wherein the substituent at the 2-position is methyl ketone.

* * * * *